United States Patent [19]

Brown et al.

[11] 4,416,761

[45] Nov. 22, 1983

[54] MULTI SLAB GEL CASTING ELECTROPHORESIS APPARATUS

[75] Inventors: Glenn E. Brown, Baltimore; Timothy P. Karpetsky, Riderwood; Phillip Jewett, Ridgely, all of Md.

[73] Assignee: The United States of America as represented by the Department of Health and Human Services, Washington, D.C.

[21] Appl. No.: 402,353

[22] Filed: Jul. 27, 1982

[51] Int. Cl.³ ............................................ G01N 27/26
[52] U.S. Cl. ............................. 204/299 R; 204/180 G
[58] Field of Search ....................... 204/180 G, 299 R; 23/230 B

[56] References Cited

U.S. PATENT DOCUMENTS

| | | | |
|---|---|---|---|
| 3,856,655 | 12/1974 | Roberts | 204/180 G |
| 3,888,759 | 6/1975 | Elson et al. | 204/299 R |
| 4,061,561 | 12/1977 | Fletcher | 204/299 R |
| 4,088,561 | 5/1978 | Anderson | 204/299 R |
| 4,130,471 | 12/1978 | Frosch | 204/180 G |
| 4,142,960 | 3/1979 | Hahn et al. | 204/299 R |
| 4,151,065 | 4/1979 | Kaplan et al. | 204/299 R |
| 4,152,242 | 5/1979 | Makonkawkeyoon | 204/299 R |
| 4,169,036 | 9/1979 | Anderson et al. | 204/299 R |
| 4,198,389 | 4/1980 | Wadsworth | 204/299 R |
| 4,224,134 | 9/1980 | Hoefer et al. | 204/180 G |
| 4,305,799 | 12/1981 | Schwartz et al. | 204/180 G |

OTHER PUBLICATIONS

Biochem J. (1980) 189, 277-284, Karpetsky et al., "Use of Polynucleotide/Polyacrylamide . . . ".
Anal. Biochem. 31, 506-511 (1969) Curtis W. Wilson "A Rapid Staining Technique . . . ".
Plant Physiol. (1971) 48, 64-68, Curtis M. Wilson, "Plant Nucleases".
FEBS Letters, vol. 51, No. 1, Mar. 1975, L. C. van Loon, "Polynucleotide-Acrylamide . . . ".
Anal. Biochemistry 58, 71-76 (1974) Zollner et al., "Human Serum Deoxyribonuclease . . . ".
Anal. Biochemistry 13, 28-42 (1965) Boyd et al., "Identification of Deoxyribonuclease . . . ".
Biochemistry 1981, 20, 2261-2267, Blank et al., "Ribonucleases of Human Serum . . . ".
Barald, Polanshek, and Jeter, Journal of Applied Chemical Biotechnology, No. 12, Dec. 1976, A Versatile and Inexpensive Apparatus for Slab Electrophoresis, pp. 735-741.

*Primary Examiner*—Howard S. Williams
*Assistant Examiner*—Terryence F. Chapman
*Attorney, Agent, or Firm*—Browdy and Neimark

[57] ABSTRACT

An electrophoresis system which provides enhanced resolution and ability to identify nucleases through use of a two-dimensional technique involving isoelectric focussing of tube gels followed by the electrophoresis of second-dimension slab gels formed by the use of a holder allowing slab gels to be cast directly on the sides of the tube gels. DNA is employed as the enzyme substrate within the slab gels. The slab gels are electrophoresed for the second dimension in a chamber wherein the rack containing a stack of slab gels forms the partition between the anolyte and catholyte compartments. After the second-dimension electrophoresis, the slab gels are incubated in incubation buffer and placed in Pyronin Y to stain the unhydrolized DNA. After staining, they are destained in acetic acid. The DNAses are then visible as colorless spots in a reddish-colored gel.

13 Claims, 5 Drawing Figures

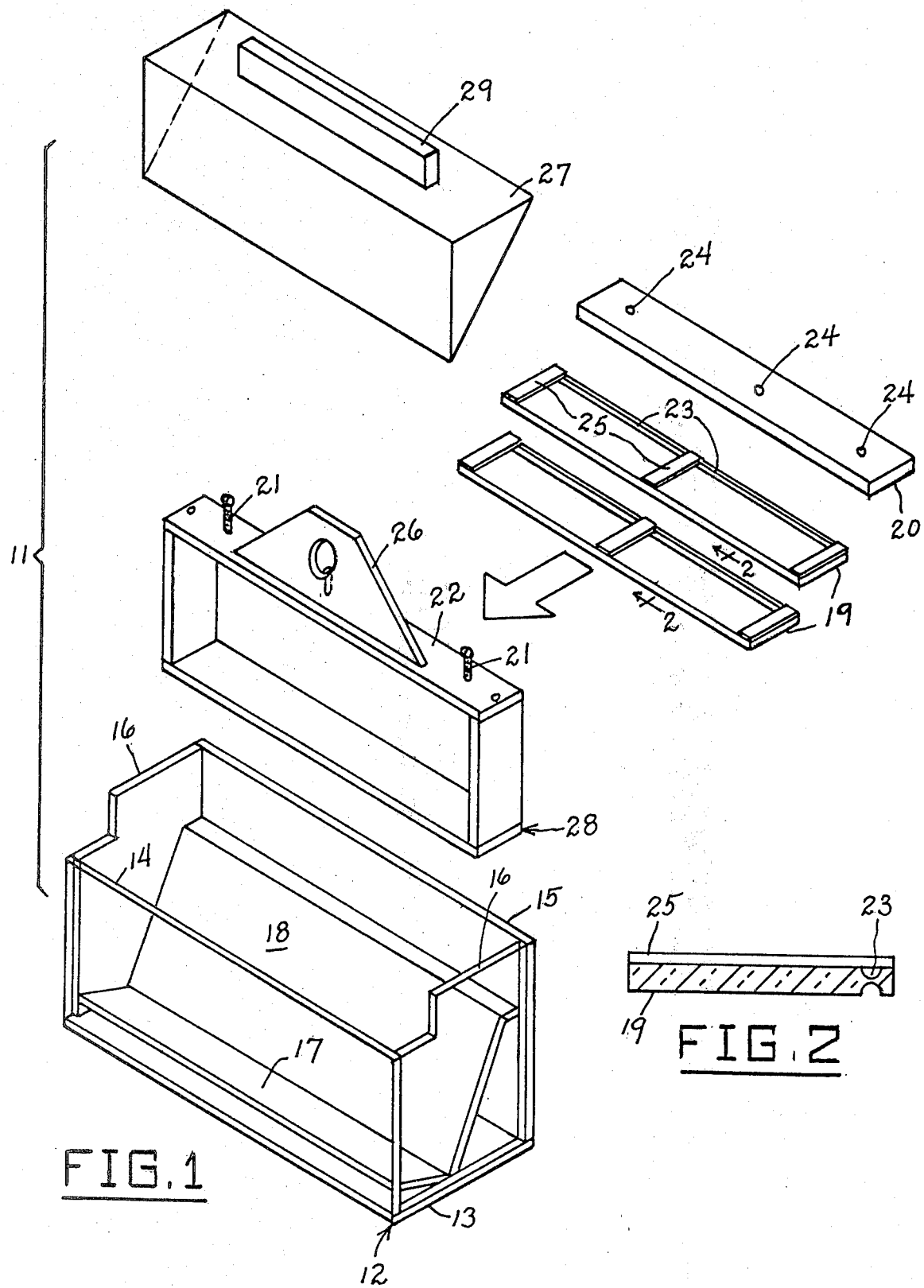

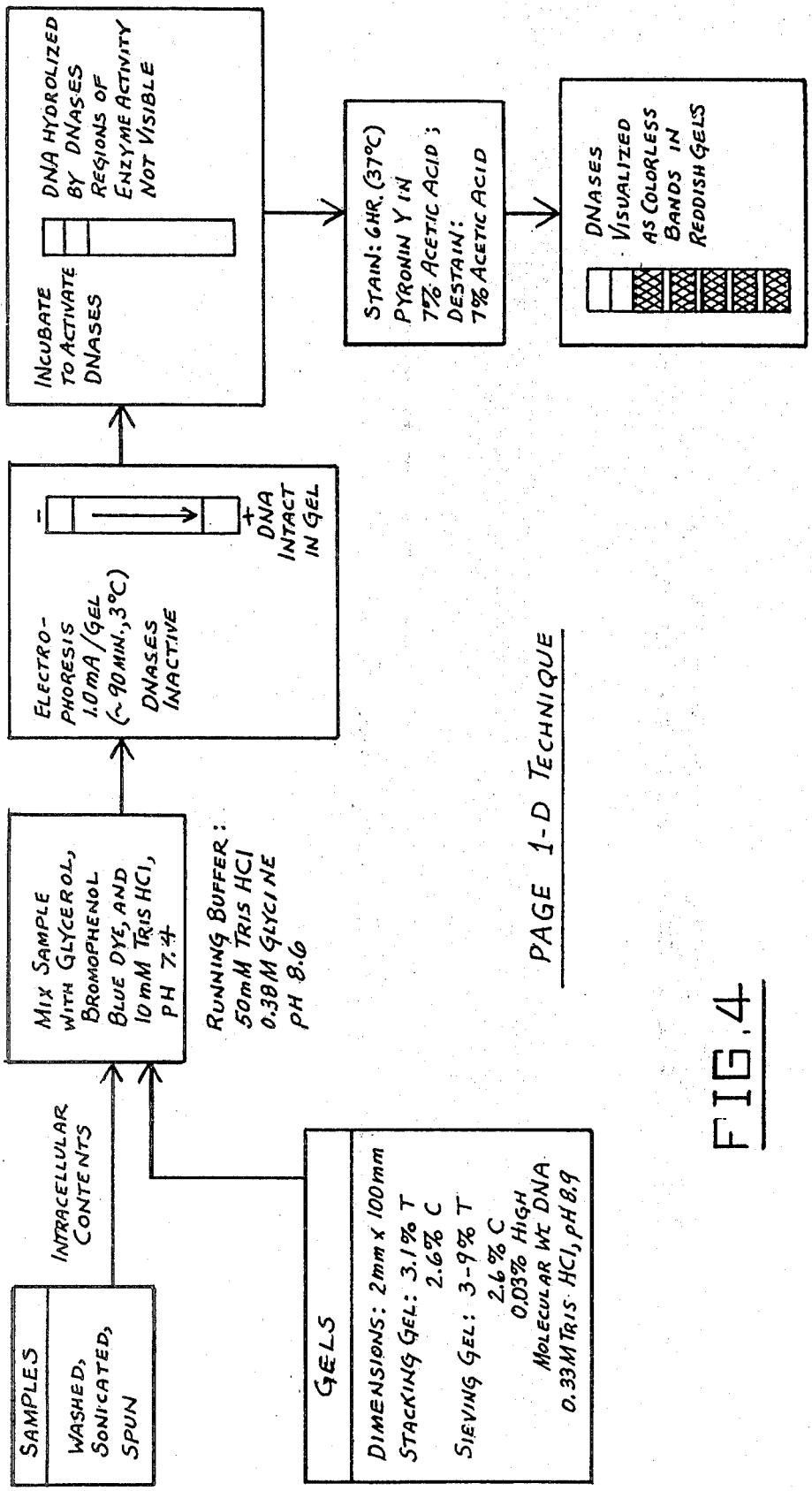

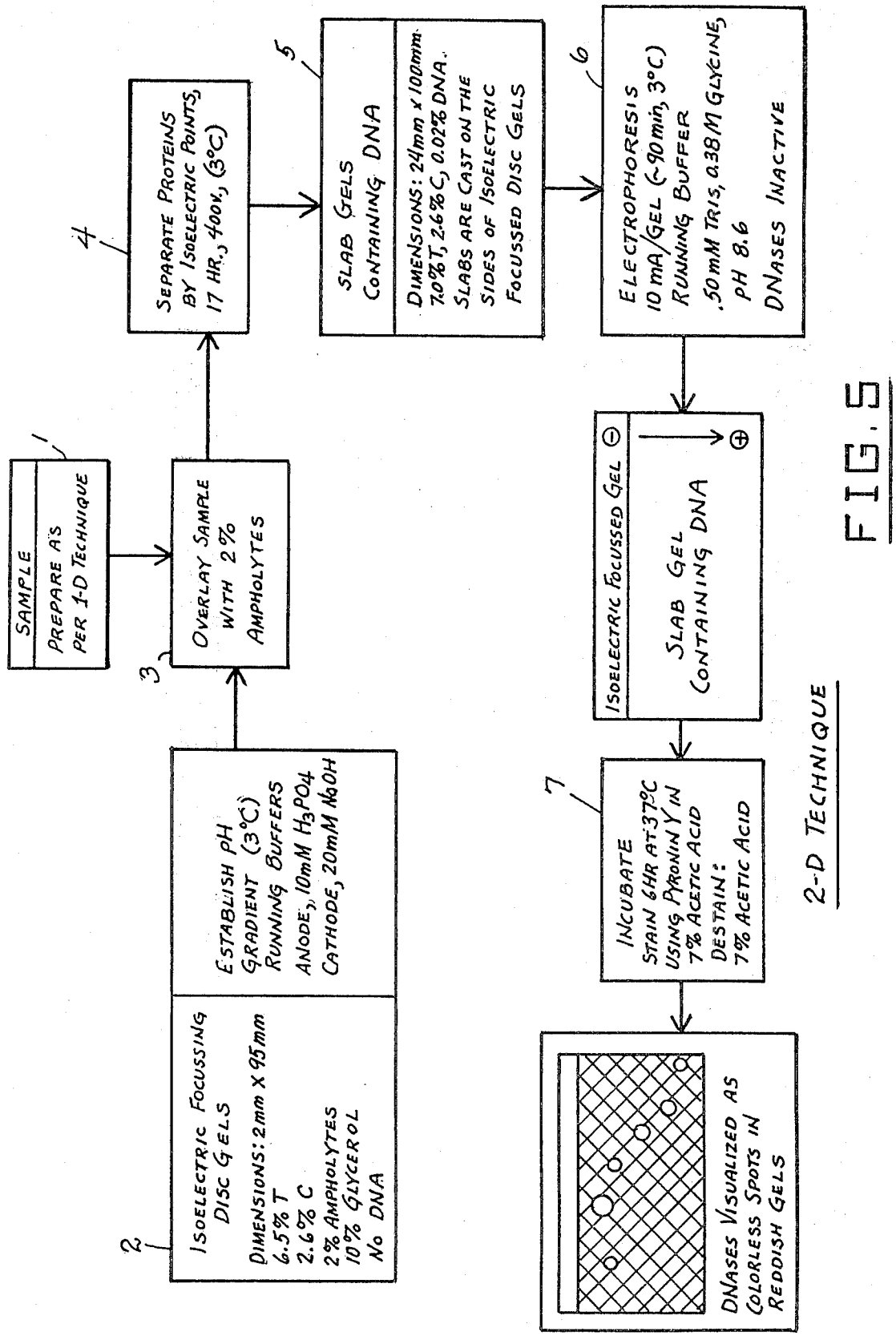

MULTI SLAB GEL CASTING ELECTROPHORESIS APPARATUS

FIELD OF THE INVENTION

This invention relates to electrophoretic procedures, and more particularly to a two-dimensional electrophoretic technique for providing two-dimensional enzyme visualization among proteins in a sample. This invention is related to one entitled "Isoelectric Focussing-Polynucleotide/Polyacrylamide Gel Electrophoresis" in the names of Karpetsky and Brown.

BACKGROUND OF THE INVENTION

Generally, electrophoresis is used to separate complex substances into their component parts by using procedures based upon the migration of electrically charged fractions in a direct current electric field. Previously, this has usually been done using a one-dimensional system in a support medium such as polyacrylamide gel with the addition of denaturing agents, such as SDS or urea, which provides a separation based on mass or on a mass-to-charge ratio.

Typical prior publications describing the one-dimensional technique include the following:

T. P. Karpetsky et al, "Use of Polynucleotide/Polyacrylamide-gel Electrophoresis as a Sensitive Technique for the Detection and Comparison of Ribonuclease Activities", (1980) Biochem. J. 189, 277-284; C. W. Wilson, "A Rapid Staining Technique for Detection of RNase after Polyacrylamide Gel Electrophoresis", (1969) Anal. Biochem., 31, 506-511; C. Wilson, "Polyacrylamide gel electrophoresis of corn ribonuclease isoenzymes", (1971) Plant Physiol., 48, 64-68; L. C. Van Loon, "Polynucleotide-acrylamide Gel Electrophoresis of Soluble Nucleases from Tobacco Leaves", (1975), FEBS Lett., 51, 266-269; E. J. Zollner et al, "Human Serum Deoxyribonuclease Assay in [$^3$H] DNA-polyacrylamide Gels without Staining Artifacts" (1974), Anal. Biochem 58, 71-76; J. B. Boyd and H. K. Mitchell, "Identification of deoxyribonucleases in polyacrylamide gel following their separation by disc electrophoresis", (1965 Anal. Biochem. 13, 28-42; A. Blank and C. A. Dekker, "Ribonucleases of human serum, urine, cerebrospinal fluid, and leukocytes. Activity staining following electrophoresis in sodium dodecyl sulfate-polyacrylamide gels", (1981) Biochemistry 20, 2261-2267.

SUMMARY OF THE INVENTION

The system of the present invention addresses the problem of enhancing the resolution of the various components in any given sample run in an acrylamide gel by using a two-dimensional system. Better resolution is obtained since the isoelectric focussing used for the first dimension involves the use of carrier ampholytes in the gel which form a pH gradient across the gel when a direct current is applied. This procedure separates protein components on the basis of their isoelectric point. The polynucleotide/polyacrylamide gel used for the second dimension separates proteins on the basis of mass and charge. The use of a two-dimensional system enhances the sensitivity so that the use of radioactive substrates previously required becomes unnecessary to locate the nuclease activity among the proteins separated.

In addition, the use of electrophoretic techniques for both dimensions using non-denaturing conditions, in contrast to previous methodology, does not destroy enzyme activity. Thus, enzyme activity may be observed either in the gel or after extraction from the gel following the completion of the electrophoresis.

The sensitivity of the system of the present invention is further increased by using a high molecular weight substrate in the gel for the second dimension rather than diffusing in a low molecular weight substrate; a substrate of too high a molecular weight will not penetrate the gel, at the completion of the electrophoresis. This eliminates the possibility that some of the sharpness of the resolution of the proteins may be lost due to diffusion or to broadening of the bands since this is a time-consuming process.

In addition, using the substrate within the gel allows for the detection of nucleases in crude samples such as serum and supernatants from sonicated cell preparations. Incubation of the gels in buffers of varying composition, pH, and ionic strength, aids in obtaining profiles of multiple enzyme activities in these samples, with the results being superior to those obtained from classical methods used to quantitate enzyme activity.

The electrophoretic technique described herein provides for enhanced resolution and ability to identify nucleases through the use of a two-dimensional electrophoretic system involving the use of isoelectric focussing of a tube gel, followed by electrophoresis in the second dimension, which uses a polyacrylamide slab gel containing polynucleotide. The second dimension slab gel is cast directly on the side of the disc gel. The gels are then incubated in incubation buffer and then placed in a suitable stain, such as Pyronin Y, to stain the unhydrolyzed polynucleotide. After staining, they are destained overnight in 7% acetic acid. The nucleases are then visible as colorless spots in a colored gel.

Accordingly, a main object of the invention is to provide an improved electrophoretic system which overcomes the deficiencies and disadvantages of the one-dimensional electrophoretic system previously employed.

A further object of the present invention is to provide an improved electrophoretic system which employs isoelectric focussing in one direction to separate proteins by isoelectric point, and subsequently uses polynucleotide/polyacrylamide gel electrophoresis to separate proteins by mass-to-charge ratio and to visualize only nuclease activities among all proteins.

A still further object of the invention is to provide an improved electrophoretic system wherein, because proteins are separated in two dimensions, the resolution of nucleases is far superior to that obtained using a one-dimensional system, wherein the sensitivity is such that it is not necessary to rely on radioactive substrates to locate enzyme activity and wherein the sensitivity is increased by using a high molecular weight substrate within the gel rather than diffusing it in as a low molecular weight substrate after electrophoresis.

A still further object of the invention is to provide an electrophoretic system of the type above mentioned, wherein DNA is employed in the procedure, and wherein DNAses are visualized as colorless spots in a colored gel having two-dimensional coordinates, permitting easy comparison with normal reference samples.

A stil further object of the invention is to provide an electrophoretic system wherein polynucleotide/polyacrylamide gel electrophoresis can be accomplished on multiple gels simultaneously in the same apparatus.

BRIEF DESCRIPTION OF THE DRAWINGS

Further objects and advantages of the invention will become apparent from the following description and claims, and from the accompanying drawings, wherein:

FIG. 1 is an exploded view, in perspective, of the components of a gel casting device employed in the two-dimensional electrophoretic system of the present invention.

FIG. 2 is an enlarged transverse vertical cross-sectional view taken substantially on line 2—2 of FIG. 1.

FIG. 4 is a flow diagram of a typical one-dimensional gel electrophoresis system.

FIG. 5 is a flow diagram of a two-dimensional gel electrophoresis system according to the pressent invention.

Figure 3:
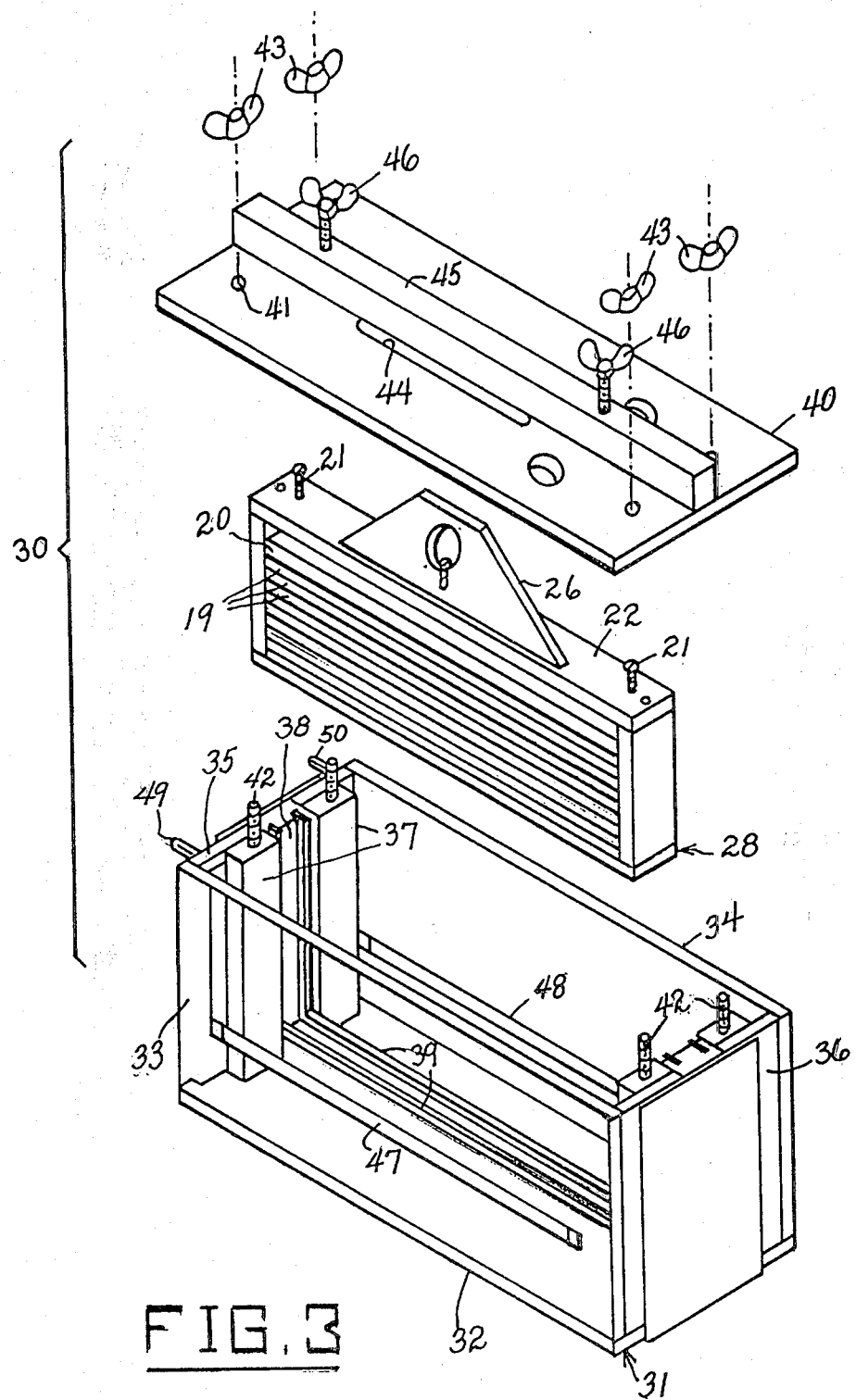
FIG. 3 is an exploded view, in perspective, of an electrophoresis chamber and a multi-slab assembled gel holder employed in the two-dimensional electrophoresis system of this invention.

For a better understanding of the invention, a possible embodiment thereof will now be described with reference to the attached drawings, it being understood that this embodiment is to be intended as merely exemplary and in no way limitative.

DETAILED DESCRIPTION OF A PREFERRED EMBODIMENT

Referring to the drawings, FIG. 4 is a flow chart generally illustrating a one-dimensional technique wherein a sample of cells is washed, sonicated and spun, after which the intracellular contents are mixed with glycerol, bromophenol blue dye and a running buffer and electrophoresed for about 90 minutes at 3° C. using a disc gel column containing DNA. During electrophoresis the DNAses are inactive and the DNA remains intact in the gel column. The material in the column is then allowed to incubate in a suitable buffer to activate the DNAses. The DNA is hydrolyzed by the DNAses, but the regions of enzyme activity are not visible. Thereafter, the disc gel column is stained for 6 hours at 37° C. by Pyronin Y in 7% acetic acid. The column is then destained in 7% acetic acid, causing the DNAses to be visualized as spaced colorless bands in a column of reddish DNA containing gels.

Referring to FIG. 5, this flow chart depicts the steps involved in obtaining two-dimensional visualization as described in the previously summarized procedure. FIGS. 1, 2 and 3 illustrate apparatus used in carrying out the two-dimensional electrophoresis method of FIG. 5. Referring to FIG. 1, 11 generally designates a casting device used for forming the slabs from the slab gel solution after the isoelectric disc gels have been processed through the first electrophoresis stage of the two-dimensional technique. The casting device 11 comprises a generally rectangular Plexiglas main housing 12 having a rectangular bottom wall 13, a front wall 14, a rear wall 15, and opposite end walls 16, 16. A forwardly and upwardly inclined shelf member 17 is rigidly secured in the bottom front portion of the housing 12, sloping rearwardly and downwardly and forming a right-angled corner with an upwardly and rearwardly inclined rigid supporting plate member 18 rigidly secured in the housing, thereby defining an inclined seat for a Plexiglas rectangular frame member 28, defining a gel holder which is slidably engageable in the housing.

The gel holding frame 28 is shaped to receive a stack of rectangular glass gel slab plates 19, being clampingly engaged by a rectangular top clamping plate 20 which is pressed downwardly by a plurality of spaced clamping screws 21 threadedly engaged through the top wall 22 of the frame 28 (see FIG. 3). Each slab plate 19 is formed with a longitudinally aligned pair of longitudinally extending disc gel-receiving grooves 23, 23 located adjacent to the rear edge of the plate 19 and on opposing surfaces, and hence being at the lowermost part of the associated slab plate 19 when the loaded frame 28 is seated in inclined position in the seat defined by right-angled plates 17, 18. Respective flat transverse Plexiglas spacer strips 25 are adhesively secured on the opposite end portions and middle portion of each glass plate 19. Clamping plate 20 is provided with recesses or indentations 24 to receive and interlock with the bottom ends of the clamping screws 21.

Rigidly secured on the top wall member 22 of frame 28 is an upstanding, longitudinally extending, flat handle flange 26. A large removable top wedge member 27 interfits between the front wall 14 and the loaded plate holder 28 to prevent formation of a large block of polyacrylamide along one side of the plate holder 28 during polymerization. Wedge member 27 is provided with a top gripping handle 29.

Referring to FIG. 3, 30 generally designates an electrophoresis chamber for performing the second-dimensional electrophoresis step on the slab gels carried in the gel holder 28 after polymerization of the slab gels on the glass plates 19, as will be presently described. The chamber 30 comprises a generally rectangular Plexiglas housing 31 having a rectangular bottom wall 32, front and rear vertical longitudinal walls 33, 34, and vertical opposite end walls 35, 36. Symmetrically secured to the inside surfaces of the opposite end walls are respective pairs of spaced vertical blocks 37, 37, defining therebetween opposite vertical guide channels 38 in which the opposite ends of the gel holder 28 are slidably receivable. A pair of spaced parallel, continuous $\frac{1}{8}''$ sponge rubber strip gaskets 39, 39 are mounted in support grooves provided therefor in the guide channels 38 and the bottom wall 32, said spaced strip gaskets being sealingly engageable with the end and bottom surfaces of the gel holder 28. A rectangular top cover plate 40 has apertures 41 to receive upstanding studs 42 provided on the top ends of the blocks 37. Wing nuts 43 are engageable on the studs 42 to lock the cover plate 40 onto the top of housing 31. Cover plate 40 is provided with a longitudinal slot 44 alongside a longitudinal gripping handle 45, said slot 44 receiving and providing clearance for the handle 26 of gel holder 28. Wings screws 46, 46 are threadedly engaged through cover plate 40 at the gripping handle 45, said wing screws being engageable with the top wall 22 of the gel holder 28 to exert downward clamping force on the gel holder 28 to insure sealing engagement thereof with the gasket strips 39, 39.

Respective anolyte and catholyte spaces are thus defined on opposite sides of the gel holder 28 when it is installed in the housing 31 as above described. Mounted in these spaces are respective electrophoresis electrodes 47, 48 supportingly secured to end wall 35 and leading to external connection prongs 49, 50 on end wall 35 for connecting the electrodes to a suitable d.c. voltage source.

Referring to FIG. 5, the two-dimensional technique begins with the sample preparation, the isoelectric focussing of the tube gel for the first dimension and the casting of the slab gel on the side of the disc gel for the second dimension. The procedure concludes with the electrophoresis of the second dimension and with the incubation and staining for the visualization of the nucleases.

In detail, in a typical procedure:

Glass tubes (110×2 mm i.d.) were soaked for a minimum of 30 minutes in Chromerge, rinsed four times in glass distilled water and given a final rinse in 95% (v/v) ethanol. The tubes were dried at 120° C. Glass plates 19 (250×25×3 mm) were washed with a mild detergent, thoroughly rinsed with water, and dried at room temperature.

Step 1:

Samples were prepared by mixing thawed cells with 10 mM Tris-HCl, pH 7.4 (sample buffer) to a concentration of $1 \times 10^6$ cells/5 μl. The samples were then sonicated for 20 sec. at 45 watts and 7° C., using a Sonicator Cell Disruptor (Model W225R, Heat Systems Ultrasonics, Plainview, N.Y.). After sonication, the samples were centrifuged in an Eppendorf Centrifuge for 5 minutes at 4° C. An aliquot of the supernatant (usually 5 μl, corresponding to the solubilized intracellular contents of $1 \times 10^6$ cells) was mixed with sample buffer to a final volume of 15 μl. To this mixture was added 2 μl of a carrier ampholine mix (1:1.5:7 mixture of pH 5-7, 40% w/v, pH 9-11, 20% w/v, pH 3.5-10, 40% w/v, LKB Instruments, Inc. Rockville, Md.), 3 μl of water, and 20 μl 0.01% w/v bromophenol blue in 85% glycerol.

Step 2:

Isoelectric focussing gels were prepared using 16 ml of distilled water, 6.5 ml of acrylamide stock (30% w/v acrylamide, 0.8% w/v bisacrylamide, Bio-Rad Laboratories, Richmond, Cal.), 1.8 ml of carrier ampholine mix, 2.85 ml glycerol, and 10 μl N,N,N',N' (tetramethylethylene-diamine, referred to as TEMED, Bio-Rad Laboratories, Richmond, Cal.). The gel solution was degassed at 12 Torr for 6 minutes. Polymerization was initiated by the addition of 1.5 ml of an ammonium persulfate solution (Bio-Rad Laboratories, Richmond, Cal.), 1% w/v in 10 mM Tris-HCl, pH 7.4. Gel tubes were filled to a height of 97 mm, and the gel was covered by an ampholine overlay solution (2% v/v carrier ampholine mix). Polymerization was complete within 30 minutes. The gels were used within two days.

Step 3:

20 μl of overlay solution was added to each gel before commencing the run. Freshly degassed catholyte (10 mM phosphoric acid) and anolyte (20 mM NaOH) were added to the upper and lower electrophoresis chambers, respectively.

Step 4:

The gels were then pre-electrophoresed at 40° C. at 200 v. for 15 minutes, 300 v. for 30 minutes, and 400 v. for 30 minutes. The catholyte was then removed, and 20 μl of sample, followed by 20 μl of ampholine overlay solution and freshly degassed catholyte were added. Electrophoresis was continued at 400 v. for 17-20 hours at 4° C.

Step 5:

Approximately 15 minutes before the isoelectric focussing was complete, the slab gel solution containing DNA was made, as follows: 100 ml distilled water, 57 ml of acrylamide stock solution, 10.53 ml of DNA stock solution (5 mg/ml stored at 4° C., Worthington Biochemical Corp., Freehold, N.J.), 52.65 ml buffer A (1.5 Tris, pH 8.9), and 88 μl TEMED. After mixing, the solution was degassed under a vacuum.

The disc gels were placed in the grooves 23 (1 mm wide and 0.5 mm deep) of the glass plates 19. The glass plates 19 were placed in the gel holder 28, which was tilted and placed in the slab casting apparatus 11 in the manner previously described.

To 200 ml of the slab gel solution was added 13.2 ml of ammonium persulfate solution. The gel solution was poured into the casting apparatus 11. Air bubbles trapped between the plates 19 were released by tapping the apparatus. The wedge member 27 was placed in the apparatus 11 against the plate holder 28 in the manner above described to prevent the formation of a large block of acrylamide.

The gel polymerized within one hour. The wedge 27 and the gel holder 28 were removed from the casting apparatus 11. The excess acrylamide was trimmed off with a razor blade.

The ends and bottom of the gel holder 28 were covered with a thin layer of high vacuum grease (Dow Corning Corp., Midland, Mich.). The holder 28 was placed in the electrophoresis apparatus 30 in tight contact with the two rubber gasket strips 39, 39. The chambers on opposite sides of the holder 28 were filled with equal volumes of 50 mM Tris-HCl and 0.38 M glycine, pH 8.6 (running buffer), and 0.01% (v/v) bromophenol blue was added to the catholyte.

Step 6:

Electrophoresis was accomplished using 12.5 mA per gel at 4° C. until the bromophenol blue traversed the width of the slab gels. After removal of the gels, one corner was marked to indicate the position of each focussed gel.

Step 7:

The gels were then incubated in either 50 mM citrate-phosphate buffer, pH 4.0, L or 100 mM Tris-HCl, pH 7.4 containing 2.5 mM $MnCl_2$ and 0.1 mM $CaCl_2$, using a volume of 50 ml/gel and placed in a shaker (Model G-25, Gyratory Shaker, New Brunswick Scientific Co., Inc. Edison, N.J.) at 37° C. Other buffers may be used to detect other types of nucleases. The buffer was changed twice at 15-minute intervals. The gels were then allowed to incubate in the buffer overnight. The buffer was removed and replaced with Pyronin Y (Bio-Rad Laboratories, Richmond, Cal.) 0.1% (w/v) in 7% (v/v) acetic acid in order to stain the unhydrolyzed DNA. After shaking for 6 hours at 37° C., the gels were destained overnight in a Bio-Rad destainer containing 7% acetic acid. The gels were placed in 50 ml conical tubes with holes cut in the sides and lids for support during the destaining procedure.

To visualize the proteins, the gels were shaken in 10% trichloroacetic acid (w/v) and 5% (w/v) sulfosalicyclic acid (fixer) for 1 hour. They were given 15-minute washes in 5% (w/v) acetic acid and 25% (v/v) methanol (destaining solution). The gels were then stained with 0.1% (w/v) Coomassie Brilliant Blue R 250 (Bio-Rad Laboratories, Richmond, Cal.) in 5% (v/v) acetic acid and 25% (v/v) methanol for 5 hours with shaking at 37° C. They were incubated in destaining solution overnight.

While specific embodiments of an improved electrophoretic technique for providing two-dimensional enzyme visualization among all other proteins in a sample and an apparatus for carrying out the technique have been disclosed in the foregoing description, it will be understood that various modifications within the scope of the invention may occur to those skilled in the art. Therefore it is intended that adaptations and modifications should and are intended to be comprehended within the meaning and range of equivalents of the disclosed embodiments.

What is claimed is:

1. A slab gel casting device for use in a two-dimensional electrophoresis system comprising a generally rectangular open frame-like rack, at least two elongated gel slab plates receivable longitudinally in said rack, the slab plate being formed adjacent one longitudinal edge thereof with grooves for receiving an elongated isoelectrically focussed polymerized disc gel to which sample is added and subsequently electrophoresed, means to clampingly hold the gel slab plates in the rack, a gel casting receptacle, supporting means in said gel casting receptacle formed to supportingly receive said rack and to support the rack in an inclined position in the receptacle, and said clamping means comprising clamping plate means receivable in said rack beneath its top portion, and means engaged in the top portion of the rack and clampingly engageable with said clamping plate means.

2. The slab gel casting device of claim 1, and wherein a plurality of said gel slab plates are provided and are stacked in said rack.

3. The slab gel casting device of claim 2, and wherein the gel slab plates are each provided on their top surfaces with a plurality of longitudinally separated spacer strips.

4. The slab gel casting device of claim 1, and an elongated blocking wedge member receivable in the gel casting receptacle between the rack and an adjacent wall of the receptacle to prevent solid polymerized material from accumulating on the rack.

5. The slab gel casting device of claim 1, and wherein said supporting means is shaped to define an L-shaped inclined seat in which the rack is substantially conformably receivable.

6. The slab gel casting device of claim 1, and a slab gel two-dimensional electrophoresis chamber formed to slidably and sealingly receive said rack and formed to define respective anolyte and catholyte compartments on opposite sides of the rack and having respective electrophoresis electrodes in said compartments.

7. The apparatus of claim 6, and wherein said electrophoresis chamber has opposite end walls provided with respective pairs of spaced vertical blocks defining channels therebetween to slidably receive the opposite ends of the rack.

8. The apparatus of claim 7, and wherein said channels and the bottom wall of the chamber are provided with a plurality of parallel inwardly projecting continuous resilient sealing strips sealingly engageable with the end and bottom surfaces of the rack.

9. The apparatus of claim 8, and wherein said chamber is provided with a top cover plate, means to clampingly secure said cover plate to the top of the chamber, and clamping screw means threadedly engaged through said top cover plate and being clampingly engageable with the top portion of the rack to exert downward sealing pressure on the rack.

10. The slab gel casting device of claim 11, wherein said clamping plate means comprises an elongated clamping plate longitudinally receivable in said rack, and said means engaged in the top portion of the rack comprising screw means threadedly engaged therein.

11. A slab gel casting device for use in a two-dimensional electrophoresis system comprising a generally rectangular open frame-like rack, at least two elongated gel slab plates receivable longitudinally in said rack, the slab plate being formed adjacent one longitudinal edge thereof with grooves for receiving an elongated isoelectrically focused polymerized disc gel to which sample is added and subsequently electrophoresed, means to clamplingly hold the gel slab plate in the rack, a gel casting receptacle, supporting means in said gel casting receptacle formed to supportingly receive said rack and to support the rack in an inclined position in the receptacle, and wherein said clamping means comprises an elongated clamping plate longitudinally receivable in said rack beneath its top portion, and screw means threadedly engaged in the top portion of the rack and being clampingly engageable with said clamping plate.

12. A slab gel casting device for use in a two-dimensional electrophoresis system comprising a generally rectangular open frame-like rack, at least two elongated gel slab plates receivable longitudinally in said rack, the slab plate being formed adjacent one longitudinal edge thereof with grooves for receiving an elongated isoelectrically focussed polymerized disc gel to which sample is added and subsequently electrophoresed, means to clampingly hold the gel slab plate in the rack, a gel casting receptacle, supporting means in said gel casting receptacle formed to supportingly receive said rack and to support the rack in an inclined position in the receptacle, and an elongated blocking wedge member receivable in the gel casting receptacle between the rack and an adjacent wall of the receptacle to prevent solid polymerized material from accumulating on the rack.

13. A slab casting device for use in a two-dimensional electrophoresis system comprising a generally rectangular open frame-like rack, at least two elongated gel slab plates receivable longitudinally in said rack, the slab plate being formed adjacent one longitudinal edge thereof with grooves for receiving an elongated isoelectrically focussed polymerized disc gel to which sample is added and subsequently electrophoresed, means to clampingly hold the gel slab plate in the rack, a gel casting receptacle, supporting means in said gel casting receptacle formed to supportingly receive said rack and to support the rack in an inclined position in the receptacle, and a slab gel two-dimensional electrophoresis chamber formed to slidably and sealingly receive said rack and formed to define respective anolyte and catholyte compartments on opposite sides of the rack and having respective electrophoresis electrodes in said compartments, said electrophoresis chamber having opposite end walls provided with respective pairs of spaced vertical blocks defining channels therebetween to slidably receive the opposite ends of the rack, said channels and the bottom wall of the chamber being provided with a plurality of parallel inwardly projecting continuous resilient sealing strips sealingly engageable with the end and bottom surfaces of the rack, and wherein said chamber is provided with a top cover plate, means to clampingly secure said cover plate to the top of the chamber, and clamping screw means threadedly engaged through said top cover plate and being clampingly engageable with the top portion of the rack to exert downward sealing pressure on the rack.

* * * * *

UNITED STATES PATENT AND TRADEMARK OFFICE
CERTIFICATE OF CORRECTION

PATENT NO. : 4,416,761
DATED : Nov. 22, 1983
INVENTOR(S) : BROWN et al.

It is certified that error appears in the above-identified patent and that said Letters Patent are hereby corrected as shown below:

Column 7, line 65, claim 10, delete "claim 11" and insert therefor --claim 1--.

Signed and Sealed this

Seventh Day of February 1984

[SEAL]

Attest:

GERALD J. MOSSINGHOFF

Attesting Officer

Commissioner of Patents and Trademarks